US010112019B2

(12) United States Patent
Dunne

(10) Patent No.: US 10,112,019 B2
(45) Date of Patent: Oct. 30, 2018

(54) DRY POWDER INHALER

(75) Inventor: Stephen T. Dunne, Suffolk (GB)

(73) Assignee: Boehringer Ingelheim Pharma GmbH & Co. KG, Ingelheim am Rhein (DE)

( * ) Notice: Subject to any disclaimer, the term of this patent is extended or adjusted under 35 U.S.C. 154(b) by 881 days.

(21) Appl. No.: 12/864,934

(22) PCT Filed: Feb. 2, 2009

(86) PCT No.: PCT/EP2009/000658
§ 371 (c)(1), (2), (4) Date: Aug. 19, 2010

(87) PCT Pub. No.: WO2009/098010
PCT Pub. Date: Aug. 13, 2009

(65) Prior Publication Data
US 2010/0326438 A1 Dec. 30, 2010

(30) Foreign Application Priority Data
Feb. 5, 2008 (GB) .................................. 0802028.1

(51) Int. Cl.
*A61M 15/00* (2006.01)

(52) U.S. Cl.
CPC ...... *A61M 15/0045* (2013.01); *A61M 15/002* (2014.02); *A61M 15/0035* (2014.02); (Continued)

(58) Field of Classification Search
CPC ........... A61M 15/002; A61M 15/0013; A61M 15/0015; A61M 15/0028; A61M 15/0035; (Continued)

(56) References Cited

U.S. PATENT DOCUMENTS 2,503,732 A * 4/1950 Heisterkamp ............ 128/203.15
5,161,524 A * 11/1992 Evans ..................... 128/203.15
(Continued)

FOREIGN PATENT DOCUMENTS

EP 0722748 A2 7/1996
WO 0100263 A2 1/2001
(Continued)

OTHER PUBLICATIONS

International Search Report, Form PCT/ISA/210, for corresponding PCT/EP2009/000658; dated May 26, 2009.
(Continued)

*Primary Examiner* — Gregory Anderson
*Assistant Examiner* — Margaret Luarca
(74) *Attorney, Agent, or Firm* — Philip I. Datlow

(57) ABSTRACT

An inhaler for use with a dry powder pharmaceutical formulation, including: a chamber containing the dry powder formulation, a valve disposed in series with the chamber for regulating air flow through the chamber, and a bypass coupled around the combination of the chamber and the valve, where the valve and bypass cooperate for ensuring that the air flow is at least essentially fixed or kept constant or at a minimum accepted or desired or required flow rate through the chamber, and for varying air flow restriction through the inhaler with flow rate, or for keeping the air flow restriction generally constant.

11 Claims, 4 Drawing Sheets

I 1 4 3 8a 8 2 8 6 8b 5

(52) U.S. Cl.
CPC .... *A61M 15/0043* (2014.02); *A61M 15/0051* (2014.02); *A61M 15/0028* (2013.01); *A61M 15/0065* (2013.01); *A61M 2202/064* (2013.01)

(58) Field of Classification Search
CPC .......... A61M 15/0043; A61M 15/0045; A61M 15/0051; A61M 15/0065; A61M 2202/064
USPC ............ 128/203.12, 203.15, 203.19, 203.21, 128/203.23, 203.24, 204.18, 204.24, 128/204.25, 205.24; 604/68–72; 251/319–321, 324
See application file for complete search history.

(56) References Cited

U.S. PATENT DOCUMENTS 5,694,920 A * 12/1997 Abrams ............ A61M 15/0028 128/200.16
5,727,546 A * 3/1998 Clarke et al. ............ 128/203.15
6,341,605 B1 * 1/2002 Ohki et al. ............... 128/203.15
6,550,477 B1 * 4/2003 Casper et al. ........... 128/203.21
6,606,992 B1 * 8/2003 Schuler et al. .......... 128/203.15
7,305,986 B1 12/2007 Steiner et al.
7,464,706 B2 * 12/2008 Steiner ............. A61M 15/0028 128/203.12
7,913,688 B2 * 3/2011 Cross et al. ............. 128/203.26
8,261,739 B2 * 9/2012 Harris et al. ............. 128/203.15
2002/0168322 A1 11/2002 Clark et al.
2004/0099266 A1 5/2004 Cross et al.
2004/0182387 A1 * 9/2004 Steiner ............. A61M 15/0028 128/203.15
2005/0268911 A1 12/2005 Cross et al.
2006/0249158 A1 11/2006 Dhuper et al.
2007/0068524 A1 3/2007 Nilsson et al.
2007/0240714 A1 10/2007 Dunne et al.
2008/0314384 A1 * 12/2008 Harris .............. A61M 15/0028 128/203.15
2010/0154794 A1 * 6/2010 Valentin ........... A61M 15/0028 128/203.15
2010/0326438 A1 12/2010 Dunne

FOREIGN PATENT DOCUMENTS

WO 2002059574 A1 8/2002
WO 03000329 A2 1/2003
WO 2006066909 A1 6/2006
WO WO 2006061637 A2 * 6/2006
WO 2007144607 A2 12/2007
WO 2007144614 A1 12/2007

OTHER PUBLICATIONS

Beitz, Wolfgang and Kuttner, Karl-Heinz, Dubbel, Taschenbuch für den Maschinenbau, 16 Ed., Springer-Verlag, New York, 3 Pages, specific reference to p. 3 (H20), right column, last illustration box. (Relevancy: The text of p. 3, right col., last illustration box translates, in order: “flow control valves; throttle valve, adjustable; and three-way-throttle-valve, adjustable.”).

* cited by examiner

DRY POWDER INHALER

BACKGROUND INFORMATION

This invention is concerned with dry powder inhalers for the delivery of drugs to the lungs. In particular, the present invention relates to an inhaler with a chamber containing a medicament or inhalation formulation in the form of powder. The powder is discharged by means of a gas or air stream flowing through the chamber to entrain the powder and to generate or form a powder spray for inhalation.

Many dry powder inhalers are on the market or have been proposed. There are two main types; passive and active. In passive devices all the energy required for deagglomeration the powder and transferring the powder to the lungs is provided by the patient. Most powder inhalers are of the passive type where the powder is inhaled by the patient without the aid of a secondary energy source.

Dry powder inhalers are subdivided into single dose devices and multi dose devices. Multi dose inhalers are further subdivided into pre metered types where the doses are stored individually in the device and metering devices where the powder dose is metered in the device.

Multi dose pre metered devices have the advantage that the single doses are metered under strict factory conditions and the powder can quite easily be isolated from the atmosphere. In many applications the active drug powder is mixed with a carrier such as lactose which tends to absorb humidity from the atmosphere which makes it stick together and difficult to de-agglomerate.

One of the main advantages of active inhalers is that the delivered mass or dose of powder is independent from the flow generated by the user which is generally accepted to be in the range of between 20 to 60 liters per minute. The disadvantage of passive inhalers that the delivered mass or dose varies according to the airflow generated by the user. The present invention is a device that minimizes variations of delivered mass or dose with airflow variations.

Metering powder inhalers have a metering chamber for accurately metering the dose to be delivered while pre metered inhalers have pre-metered doses in capsules or blister or other chambers. For simplification both types will be called metering chambers in this specification. Most passive powder inhalers have a primary flow path for the air that goes through the metering chamber and carries the powder to the patient and a secondary flow path or bypass where the air does not go through the powder-metering chamber.

When the airflow through the chamber containing the powder varies, deagglomeration of the powder and spray generation vary as well. Consequently, the spray characteristics and the amount of outputted powder may very significantly.

SUMMARY

Object of the present invention is to provide an inhaler with improved discharge characteristics.

The above object is achieved by an inhaler according to claim 1. Preferred embodiments are subject of the subclaims.

According to the present invention, the inhaler comprises at least one valve for regulating flow through the chamber with powder, for ensuring that airflow is at least essentially fixed through the chamber, for varying the airflow restriction with flow rate, and/or for keeping the airflow restriction generally constant. This allows to improve the discharge characteristics, in particular in passive inhalers where the discharge characteristics of the inhaler greatly depend on the breathing in of the respective user or patient, i.e. of the total flow rate of air through the inhaler.

In particular, the present invention relates to a valve that keeps the airflow through the metered drug formulation at least essentially constant ensuring a constant delivery of powder to the patient. To do this the valve is dimensioned so that at the minimum accepted flow rate (20 liters/minute) enough air reaches the metering chamber. For devices with bypasses as the flow rate increases with different users or even with the same user more air is forced to go via the bypass.

For devices with bypasses the valve may be located in the primary flow path or the bypass. When in the primary flow path the valve restricts flow or closes with increased total flow and if in the by pass the reverse happens. For inhalers with by passes the device may have a valve in both the primary and by pass flow paths.

With devices with bypasses the pressure drop or restriction across the device is kept generally constant.

For devices without bypasses the valve is located in the primary flow path. In this case the device flow restriction varies with flow rate.

The valve may be operated automatically or pre adjusted by the user or other depending on the inhalation capacity of the user.

Preferably the valve or valves are located upstream of the powder chamber to eliminate powder losses on valve surfaces.

Many valve types may be used; spring loaded plungers, electronic controlled valves, rubber slit valves that close or open with increasing flow pressure or any other type of flow regulating valve.

BRIEF DESCRIPTION OF THE DRAWINGS

Further aspects and features of the present invention will be apparent from the claims and from the following description referring to the drawings. In the drawings, it shows:

DETAILED DESCRIPTION

In the following, not all possible embodiments are shown. It must be understood that other embodiments are possible based on the invention.

Figure 1:
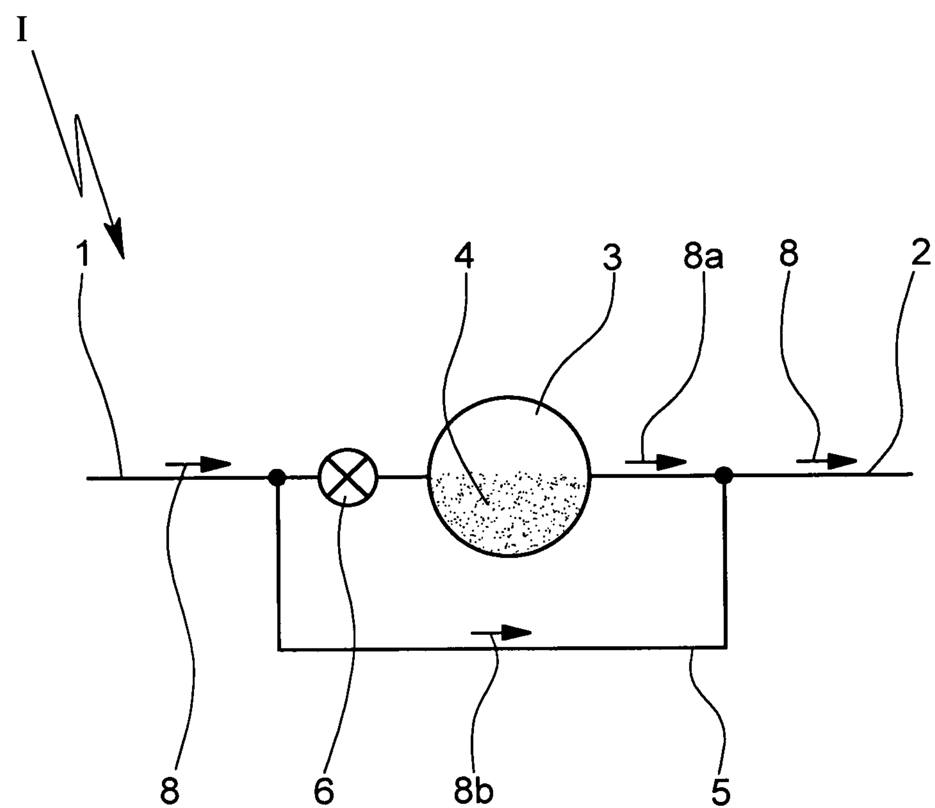
FIG. 1 a schematic diagram of an inhaler according to a first embodiment of the present invention.

In FIG. 1 a schematic of an inhaler I with a valve 6 in a primary flow path is shown. Air is drawn into the inhaler I via an inlet 1 of the inhaler I and delivered to the patient at point 2. A metering chamber 3 has powder 4 within. A bypass 5 connects inlet 1 to outlet 2.

The inhaler I comprises the inlet 1 where air can be drawn into the inhaler I. At least part of the air can flow through the chamber 3 containing the powder 4 (to entrain and discharge the powder 4). The mixture of air and powder is discharged via point 2 which represents in particular an outlet or nozzle of the inhaler I.

Figure 4:
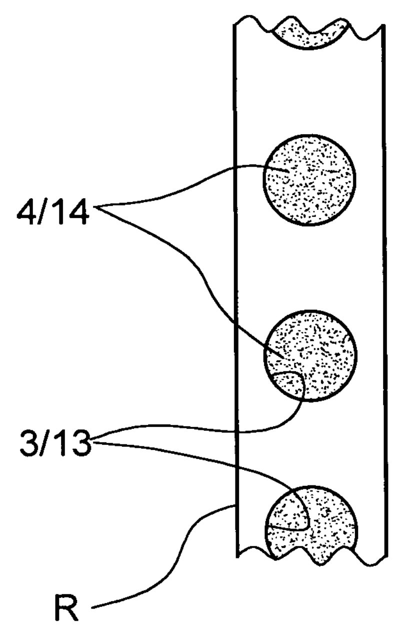
FIG. 4 a schematic view of a reservoir for an inhaler according to the present invention.

The chamber 3 may contain a pre-metered dose of the powder 4 or may be used to meter the powder 4 in particular of a bulk storage of powder 4 (not shown). The inhaler I may comprise multiple chambers 3 with pre-metered doses of powder 4 and/or a reservoir R as shown in FIG. 4, in particular a blister strip or carrier with multiple chambers 3 respectively containing a dose of the powder 4.

The total flow 8 generated by the patient is split between the primary flow 8*a* and bypass flow 8*b*. A valve 6 ensures that flow 8*a* through the chamber 3 is at least essentially fixed by restricting flow 8*a* and increasing flow 8*b* when total flow 8 increases.

The primary flow 8*a* is the part of the total flow 8 of air that is flowing through the chamber 3. The bypass flow 8*b* is the other part of the total flow 8 of air that is flowing through the bypass 5.

The valve 6 is located streamup of the chamber 3 in the primary flow path, i.e. in the flow path of the chamber 3. The bypass 5 branches from the main flow path coming from inlet 1 streamup of valve 6. However, other arrangements are possible as well. The valve 6 may be adjusted by the user or any other person or be an automatic valve such as described in FIG. 3.

Preferably, the inhaler I or valve 6 is dimensioned or constructed such that the primary flow 8*a* is kept or regulated at least essentially to a desired or required (minimum) primary flow rate 8*a* of air through the chamber 3. This desired or required primary flow rate is in particular less than 30 liters/min, in particular about 20 liters/min.

If the user or patient draws more air through the inhaler 1, i.e. if the total flow rate 8 is higher, the amount exceeding the required or desired primary flow rate 8*a* is at least essentially directed as bypass flow 8*b* through the bypass 5 in the shown embodiment.

Preferably, the inhaler I or valve 6 is constructed or dimensioned such that the pressure drop over the inhaler I (i.e. between inlet 1 and outlet 2) is kept at least essentially constant.

It is also possible to omit the bypass 5. In this case, the valve 6 preferably significantly increases the total flow restriction, i.e. the flow restriction of the inhaler 1, when the desired or required primary flow rate 8*a* through the chamber 3 is approached or reached or exceeded. Thus, the airflow through the chamber 3 and the total airflow can be kept essentially or better constant than without valve 6.

In the following, a second embodiment of the inhaler I will be explained with reference to FIG. 2. The previous description applies preferably in a similar manner even if not repeated.

Figure 2:
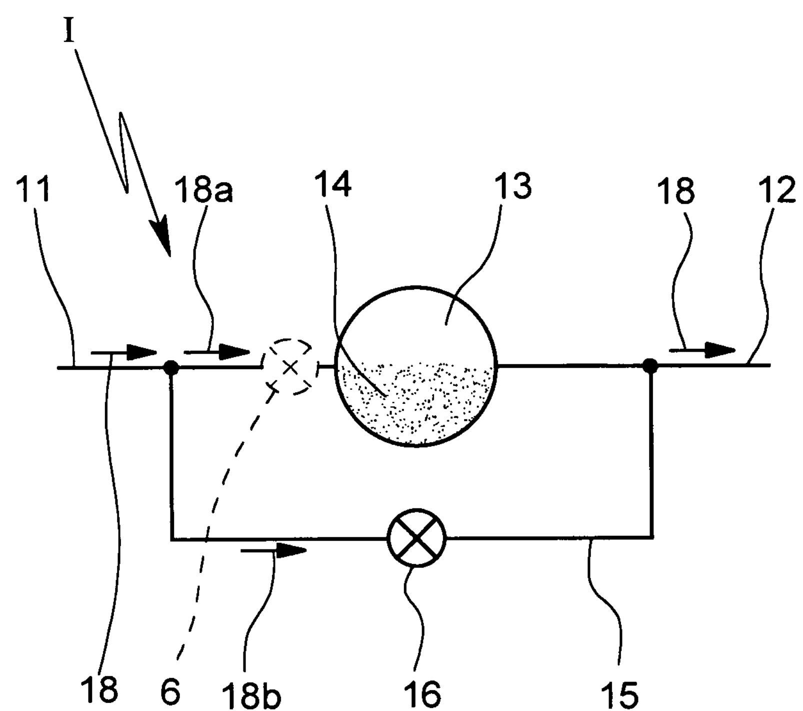
FIG. 2 a schematic diagram of an inhaler according to a second embodiment of the present invention.

In FIG. 2 shown a schematic view of an inhaler I with a valve 16 in the bypass flow path. Air is drawn into the inhaler via inlet 11 and delivered to the patient at point 12. A metering chamber 13 has powder 14 within. A bypass 15 connects inlet 11 to outlet 12. The total flow 18 generated by the patient is split between the primary flow 18*a* and bypass flow 18*b*. The valve 16 ensures that flow 18*a* through the chamber 13 is fixed by restricting flow 18*b* through the bypass 15 when total flow 18 decreases. The valve 16 may be adjusted by the user or any other person or be an automatic valve.

The second embodiment can behave similar to the first embodiment with bypass 5.

It is also possible to provide a valve 6 in the primary flow path in addition to the valve 16 in the bypass path as shown by dashed lines in FIG. 2. Thus, an even better control of the flow rates is possible.

The valve 6 or 16 may be a (automatic) flow regulating valve or (depending on the flow characteristics of the inhaler I or the construction with or without bypass 5/15) a pressure regulating valve.

Figure 3:
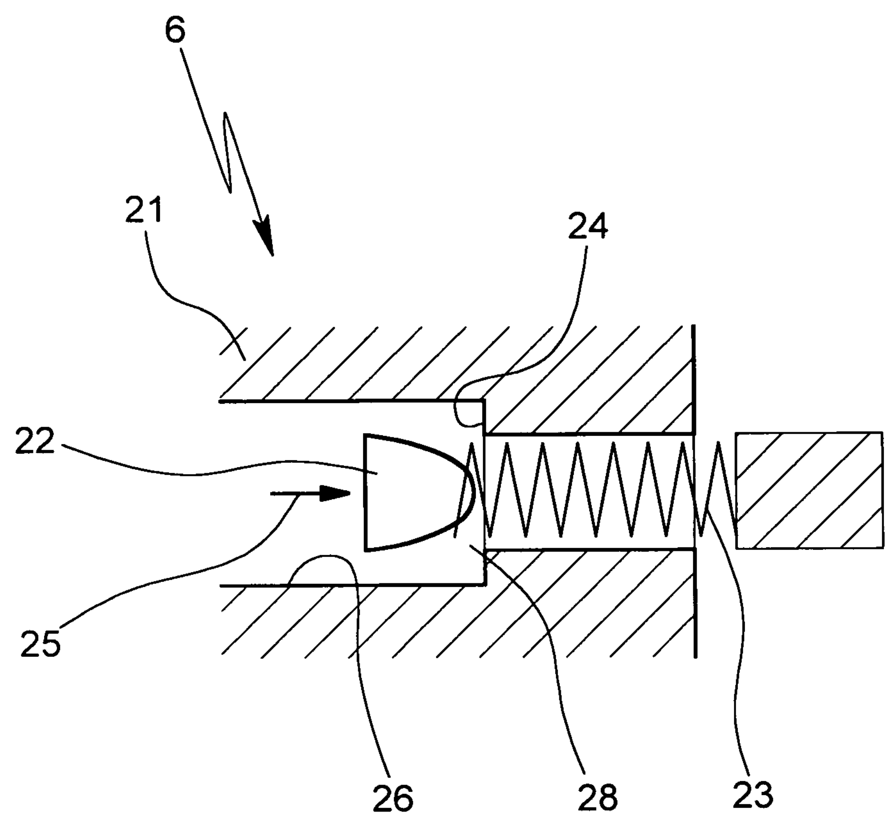
FIG. 3 a schematic representation of a valve for an inhaler according to the present invention.

In FIG. 3, an example of the automatic flow regulating valve 6 is shown for use in the primary airflow 8*a* or 18*a*. A body 21 of the valve 6 has a passageway 26 with a shoulder 24. A preferably conical plunger 22 is moveable and/or mounted on a spring 23. The plunger 22 forms a gap 28 between shoulder 24 and plunger 22. The air flows in the direction of arrow 25. As the airflow 25 tries to increase pressure on plunger 22, this forces the plunger 24 to move towards shoulder 24 closing gap 28 restricting the flow and keeping it relatively constant at all times.

Preferably, the inhaler I and/or the valve 6/16 work only mechanically. However, it is also possible that the valve 6 or 16 work electronically or in any other manner.

The inhaler I and/or the valve 6/16 may be constructed or dimensioned such that the primary air flow 8*a* through the chamber 3/13 is allowed or opened only if a sufficiently high suction force, air pressure and/or bypass air flow 8*b*/18*b* is present or detected.

FIG. 4 shows in a very schematic view a reservoir R of the inhaler I. Preferably, the reservoir can be inserted into the inhaler I. The reservoir R comprises multiple chambers 3/13 respectively containing a dose of powder 4/14. The reservoir R is preferably a blister strip wherein the chambers 3/13 are formed by blisters which can be opened preferably by peeling or piercing and/or one after the other in the inhaler I. However, other constructional solutions are possible as well.

The invention claimed is:

1. An inhaler (I), comprising:

an inlet into which air is drawn, an outlet through which air exits, a pharmaceutical medicament formed of a loose, dry powder formulation for suspension in the air and being entrained by an air flow of the air generated passively, by which a patient draws the air via inhalation to create the air flow and a resultant aerosol, a chamber (3, 13) containing a pre-metered amount of the dry powder formulation (4, 14), which is in fluid communication with the inlet and the outlet, such that at least some of the air is received from the inlet into the chamber to entrain substantially all of the pre-metered amount of the dry powder formulation and to carry the pre-metered amount of the dry powder formulation out through the outlet, a valve (6) disposed in series with the chamber for varying an extent to which the air flow (8*a*, 18*a*) through the chamber (3, 13) may flow, and a bypass (5, 15) coupled from the inlet around the combination of the chamber and the valve, to the outlet such that a total air flow is equal to the air flow through the chamber plus an air flow through the bypass, where the bypass (5, 15) permits at least some of the air to bypass the chamber (3, 13) and permits splitting the total air flow between a primary flow (8*a*, 18*a*) through the valve and chamber, and a bypass flow (8*b*, 18*b*) through the bypass, wherein the valve (6) is located in the primary flow such that the valve (6) closes with increased total flow such that the valve and bypass cooperate for ensuring that the air flow through the bypass increases as the total air flow increases such that the primary flow (8*a*, 18*a*) through the chamber is at least essentially fixed or kept constant through the chamber (3, 13).

2. The inhaler according to claim 1, wherein the inhaler (I) is constructed such that the air is drawn via the inlet (1, 11) and delivered via the combined valve and chamber (3, 13) to the outlet (2, 12).

3. The inhaler according to claim 1, further comprising a further valve (16) disposed in the bypass (5, 15), such that the further valve (16) restricts flow or closes with decreased total flow.

4. The inhaler according to claim 1, wherein the valve and the bypass cooperate such that more air is forced to go via the bypass (5, 15) as the total flow rate increases.

5. The inhaler according to claim 1, wherein the valve and bypass cooperate such that a pressure drop or restriction across the inhaler (I) is kept generally constant.

6. The inhaler according to claim 1, wherein the valve (6) is located upstream of the chamber (3, 13).

7. The inhaler according to claim 1, wherein the valve (6) is a flow regulating valve.

8. The inhaler according to claim 1, wherein the inhaler (I) comprises pre-metered doses of the powder (4, 14) in chambers (3, 13), which include at least one of capsules, blisters, and a reservoir (R).

9. The inhaler according to claim 1, wherein the valve (6) comprises a plunger (22) that is biased by means of a spring (25) so that the valve (6) can be closed or restrict the air flow through the valve (6) when the air flow increases the pressure on the plunger (22).

10. An inhaler (I), comprising:

an inlet into which air is drawn, an outlet through which air exits, a pharmaceutical medicament formed of a loose, dry powder formulation for suspension in the air and being entrained by an air flow of the air generated passively, by which a patient draws the air via inhalation to create the air flow and a resultant aerosol, a chamber (3, 13) containing a pre-metered amount of the dry powder formulation (4, 14), which is in fluid communication with the inlet and the outlet, such that at least some of the air is received from the inlet into the chamber to entrain substantially all of the pre-metered amount of the dry powder formulation and to carry the pre-metered amount of the dry powder formulation out through the outlet, a valve (6) disposed in series with the chamber for varying an extent to which the air flow (8*a*, 18*a*) through the chamber (3, 13) may flow, and a bypass (5, 15) coupled from the inlet around the combination of the chamber and the valve to the outlet such that a total air flow is equal to the air flow through the chamber plus an air flow through the bypass, wherein the valve and bypass cooperate for ensuring that the air flow through the bypass increases as the total air flow increases such that the air flow (8*a*, 18*a*) through the chamber is at least essentially fixed or kept constant through the chamber (3, 13), wherein the valve is pre-adjustable to set the air flow through the chamber to match an inhalation capacity of a user, and wherein the valve (6) comprises a plunger (22) that is biased by means of a spring (25) so that the valve (6) can be closed or restrict the air flow through the valve (6) when the air flow increases the pressure on the plunger (22).

11. An inhaler (I), comprising:

an inlet into which air is drawn, an outlet through which air exits, a pharmaceutical medicament formed of a loose, dry powder formulation for suspension in the air and being entrained by an air flow of the air generated passively, by which a patient draws the air via inhalation to create the air flow and a resultant aerosol, a chamber (3, 13) containing a pre-metered amount of the dry powder formulation (4, 14), which is in fluid communication with the inlet and the outlet, such that at least some of the air is received from the inlet into the chamber to entrain substantially all of the pre-metered amount of the dry powder formulation and to carry the pre-metered amount of the dry powder formulation out through the outlet, a valve (6) disposed in series with the chamber for varying an extent to which the air flow (8*a*, 18*a*) through the chamber (3, 13) may flow, and a bypass (5, 15) coupled from the inlet around the combination of the chamber and the valve, to the outlet such that a total air flow is equal to the air flow through the chamber plus an air flow through the bypass, where the bypass (5, 15) permits at least some of the air to bypass the chamber (3, 13) and permits splitting the total air flow between a primary flow (8*a*, 18*a*) through the valve and chamber, and a bypass flow (8*b*, 18*b*) through the bypass, wherein the valve (6) is located in the primary flow such that the valve (6) at least one of restricts flow and closes with increased total flow such that the valve and bypass cooperate for ensuring that the air flow through the bypass increases as the total air flow increases such that the primary flow (8*a*, 18*a*) through the chamber is at least essentially fixed or kept constant through the chamber (3, 13), and wherein the valve (6) comprises a plunger (22) that is biased by means of a spring (25) so that the valve (6) can be closed or restrict the air flow through the valve (6) when the air flow increases the pressure on the plunger (22).

* * * * *